(12) United States Patent
Cors et al.

(10) Patent No.: US 9,335,200 B2
(45) Date of Patent: May 10, 2016

(54) METHOD AND APPARATUS FOR DETECTING PHASE BOUNDARIES AND CORRESPONDINGLY EQUIPPED LABORATORY DEVICE

(75) Inventors: Nicolas Cors, Stafa (CH); Markus Schoni, Nanikon (CH); Markus Wiggli, Tann (CH); Adi Zuppiger, Siebnen (CH)

(73) Assignee: TECAN TRADING AG, Mannedorf (CH)

( * ) Notice: Subject to any disclaimer, the term of this patent is extended or adjusted under 35 U.S.C. 154(b) by 661 days.

(21) Appl. No.: 13/504,379

(22) PCT Filed: Dec. 22, 2010

(86) PCT No.: PCT/EP2010/070599
§ 371 (c)(1),
(2), (4) Date: Jun. 14, 2012

(87) PCT Pub. No.: WO2011/080199
PCT Pub. Date: Jul. 7, 2011

(65) Prior Publication Data
US 2012/0242354 A1    Sep. 27, 2012

(30) Foreign Application Priority Data
Dec. 30, 2009   (CH) ...................................... 2011/09

(51) Int. Cl.
*G01F 23/26*    (2006.01)
*G01N 35/10*    (2006.01)

(52) U.S. Cl.
CPC ............ *G01F 23/268* (2013.01); *G01F 23/266* (2013.01); *G01N 35/1011* (2013.01); *G01N 2035/1025* (2013.01)

(58) Field of Classification Search
CPC . G01F 23/266; G01F 23/268; G01N 35/1011; G01N 2035/1025
USPC .................................................. 324/672, 663
See application file for complete search history.

(56) References Cited

U.S. PATENT DOCUMENTS

| | | | |
|---|---|---|---|
| 2003/0069051 A1* | 4/2003 | Pretre et al. .................... | 455/572 |
| 2005/0092080 A1* | 5/2005 | Harazin et al. .............. | 73/290 R |
| 2009/0071245 A1* | 3/2009 | Harazin et al. .............. | 73/290 R |
| 2010/0301878 A1* | 12/2010 | Armbruster et al. .......... | 324/676 |

FOREIGN PATENT DOCUMENTS

DE          102007061573       * 12/2007 .................... 324/676

* cited by examiner

*Primary Examiner* — Melissa Koval
*Assistant Examiner* — Courtney McDonnough
(74) *Attorney, Agent, or Firm* — Notaro, Michalos & Zaccaria P.C.

(57) ABSTRACT

A device for detecting a phase boundary in a liquid tank a sensor that can be advanced in the direction of the phase boundary in the liquid tank. A circuit processes an output signal of the sensor to detect a change in capacitance and has a first channel with a first filter module to filter out a first signal having a short pulse width from the output signal and a second channel having a second filter module to filter out a second signal having a greater pulse width from the output signal. A controller module with comparator module determines whether the first signal reaches a first threshold value and a processing module determines whether the second signal meets predefined second signal criteria.

21 Claims, 7 Drawing Sheets

METHOD AND APPARATUS FOR DETECTING PHASE BOUNDARIES AND CORRESPONDINGLY EQUIPPED LABORATORY DEVICE

The invention relates to methods and apparatuses for detecting a phase boundary and a respectively equipped laboratory device. In particular, laboratory devices are concerned which are arranged for detecting a liquid level in a liquid container.

The priority of the Swiss patent application CH 02011/09 is claimed, which was filed on 30 Dec. 2009.

BACKGROUND OF THE INVENTION

There are numerous laboratory systems and medical and pharmaceutical devices where it is important to determine the filling level in test tubes, titre plates or the like. There are also applications which concern the detection of liquid-liquid phase boundaries. The term of phase boundary shall be used below both for transitions between gaseous and liquid media (gas-liquid phase boundary) and for transitions between different liquid media (liquid-liquid phase boundary).

Such a determination of phase boundaries is especially relevant when the automation of measuring or test procedures is concerned. The determination of the filling level typically occurs by means of a detection of the liquid level, i.e. the position of the phase boundary between air and liquid is determined. This process is also known as "Liquid Level Detection" (LLD).

Liquid level detection is used in pipetting devices for example. In this case, the pipetting needle should enter the liquid to be pipetted as little as possible when asperating with a pipette in order to keep the contamination with the sample liquid as low as possible. As a result, the pipetting needle is therefore typically submerged only 2 mm beneath the liquid level during the asperating in order to ensure that the pipetting needle has been sufficiently submerged and therefore no air can be drawn in. During the asperation process, the pipetting needle will then continuously follow the decreasing liquid level, so that it always remains submerged with the same depth with respect to the liquid level. After the asperation the height can be calculated on the basis of the aspirated volume and the cross-sectional area of the liquid container where the gas-liquid phase boundary should be located. When the tip of the pipette emerges from the fluid, an emerging signal can be compared with the calculated position of the gas-liquid phase boundary in order to thereby verify the pipetting process. Since a gas and a liquid have considerably different dielectric constants, the gas-liquid phase boundary can be determined by way of a change in capacitance.

The detection of the liquid-liquid phase boundary plays an important role in a liquid-liquid extraction for example. In the liquid-liquid extraction, the different solubility of substances in two solvents which are not miscible with one another will be utilised. One hydrophilic phase (mostly water) and one hydrophobic organic solvent are respectively used as solvents. After the extraction, the phase with the expected substance will be removed by pipetting. It is often important to know the precise phase boundary between aqueous and organic phase in order to avoid inadvertently pipetting from the other phase. Since non-miscible liquids have clearly different dielectric constants, the liquid-liquid phase boundary can be determined by way of a change in capacitance. This can be used for example for removing an intermediate phase by pipetting for example.

In recent years laboratory appliances have become more precise and more complex. The trend goes in the direction of high integration, automation and parallelism. This leads to a high spatial densification of the individual components. This densification not only leads to mechanical and other constructional problems, but also those with respect to the position of the electronic evaluation capability, whereby the mutual influence of adjacent measuring channels and other aspects can lead to problems.

The detection of a phase boundary is typically performed in a capacitive way, as schematically shown in FIG. 1. FIG. 1 shows the arrangement of a known laboratory appliance 100 which is configured in this case for detecting a liquid level. The presence of a liquid 1 or the phase boundary between air and liquid 1 is detected in this case by the observance of a change in capacitance $C_{tip/liq}$. An electronic charging/discharging circuit 2 ensures charging and discharging in order to enable the measurement of the effective capacitance between a sensor in the form of a pipette tip 3 for example and a grounded base plate 4. Signal processing can occur with a signal processing circuit 7 which is supported by a controller 8 for example.

The mode of operation of the laboratory appliance 100 can differ depending on the capacitance measuring method. An excitation with a sine signal can occur for example by the charging/discharging circuit 2 in order to measure a signal phase displacement with the signal processing circuit 7 and the controller 8, which signal phase displacement is representative of the magnitude of the capacitance. It is also possible to charge a capacitance via a resistor by means of another charging/discharging circuit 2 and then perform a direct discharge of the capacitance via a transistor such as an FET transistor (field-effect transistor).

A further capacitance measuring method would be the formation of an oscillation circuit which consists of a coil and the measuring capacitance and in which the resonant frequency of the oscillation circuit is evaluated which decreases with the increase of the capacitance.

The effective capacitance which results depending on the laboratory appliance 100 from the stray capacitances, electrical couplings by the sensor or the pipette tip 3, the conductivity of the liquid 1 and the crosstalk between adjacent measuring channels (known as next tip in FIG. 1) is very low. It typically lies in the range of a few picofarads (pF). The change in capacitance $C_{tip/liq}$ which is obtained during immersion from air into a liquid is again smaller approximately by a factor of 100 to 1000.

Signal processing circuits 7 were typically used until now for the detection of phase boundaries, which signal processing circuits evaluate a short bounce in the measured output signal s(t), which is obtained for example when the sensor 3 penetrates a phase boundary (which in this case is during the immersion into the liquid 1).

It is problematic that the change in capacitance $C_{tip/liq}$ to be measured can hardly be recognised in the measured output signal s(t), because in this case stray capacitances such as $C_{tip/tip}$ which originate from crosstalk of adjacent channels and changes in capacitance superimpose one another as a result of moving electrical feed lines.

It is desirable with the increasing degree of automation of the laboratory appliances to arrange the respective procedures in such a way that only little manual intervention is required. It needs to be taken into account that numerous situations can occur in automated pipetting systems or appliances which cannot be solved automatically by current automatic pipetting systems or appliances.

It is therefore the object of the invention to provide an apparatus and a method for detecting a phase boundary which enable secure detection of the phase boundary every time. Furthermore, the invention relates to providing a respective laboratory appliance.

The method and the apparatus or the laboratory appliance shall preferably be arranged in such a way that it automatically recognises critical situations or special cases and therefore does not require any manual or mechanical intervention.

These objects are achieved in accordance with the invention by a method according to claim 1, apparatus according to claim 10 and a laboratory appliance according to claim 18.

The method in accordance with the invention is characterised by the characterising features of claim 1. The apparatus in accordance with the invention is characterised by the characterising features of claim 11, and the laboratory appliance in accordance with the invention is characterised by the characterising features of claim 19.

In an especially preferred embodiment of the invention, charging and discharging is performed in an alternating fashion while the sensor is moved forward in the direction towards the phase boundary to be detected. When the phase boundary is reached (e.g. a liquid level) a change in capacitance is obtained which is evaluated by processing an output signal. Within the scope of this processing, which shall also be referred to herein as evaluation or signal evaluation, there will be a separation of the output signal by means of a first filter and a second filter. The first filter supplies a first signal of short pulse width and the second filter a second signal of larger pulse width. It is determined on the basis of these two signals whether the first signal fulfils at least one predetermined first signal criterion (e.g. threshold value and/or pulse width and/or ascending gradient). It is determined on the other hand whether the second signal fulfils at least one predetermined second signal criterion (e.g. threshold value and/or pulse width and/or ascending gradient and/or monotonous ascending gradient over several measuring points). If the first and second signal criteria are fulfilled, an identifier (e.g. in the form of a signal or a special code) is output which is representative of all displays of a detection of a liquid level.

The invention is arranged to perform relative capacitance measurements or evaluations since numerous disturbance and influencing quantities such as the depth of the current immersion position have little or no influence under relative consideration. A relative capacitance measurement or evaluation leads to considerably more robust and repeatable results. The determination of absolute capacitance values for the detection of phase boundaries is very laborious because signals are smaller by several magnitudes when passing through a phase boundary than the actual capacitance values of the apparatus. Moreover, absolute statements are rendered more difficult in such a way that the entire environment is "floating" from the standpoint of signal processing.

In accordance with the invention, a slow signal and a fast signal are electronically evaluated. The fast signal can be used as a "waking" signal. If the fast signal meets a first criterion, e.g. it exceeds the first threshold value, it is assumed that there is a valid detection and further method steps will follow. More precise evaluations are then performed on the basis of an evaluation/processing of the slow signal. Electrostatic disturbances can therefore be "filtered out" for example since a faster first signal can occur in case of electrostatic disturbances, but no slow second signal will occur which would indicate a "real" detection.

It is an advantage of the present invention that the slow signal permits a number of statements which would otherwise only be obtainable from an absolute measured signal.

The invention allows providing universal apparatuses and laboratory appliances which supply reliable detection results under a large variety of situations and under a large variety of preconditions.

The apparatus in accordance with the invention, the laboratory appliance in accordance with the invention and the method in accordance with the invention will be explained below in closer detail by reference to exemplary embodiments shown in the schematic drawings which do not limit the scope of the invention.

Figure 1:
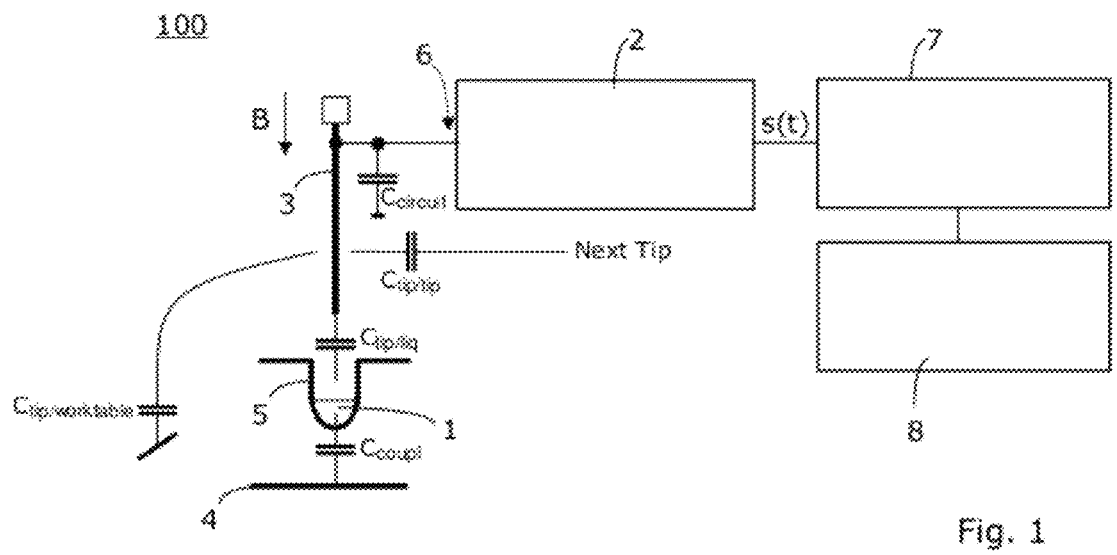
FIG. 1 shows a schematic side view of a laboratory appliance according to the state of the art.

Advantageous embodiments of the invention will be described below, with said embodiments concerning examples. They comprise both different configurations of the entire invention and also assemblies and individual parts of the invention. The described assemblies and individual parts of the various embodiments can principally be combined with one another, or the assemblies and individual parts of individual embodiments can be replaced by the assemblies and individual parts of other embodiments. The combinations formed thereby can require minor adjustments that are well known to the person skilled in the art and will therefore not be described below in closer detail, e.g. for the purpose of cooperation or engagement of the assemblies and individual parts into each other.

The term of phase boundary will be used for boundaries between 2 or more media which have different dielectric constants. In particular, liquid-liquid and gas-liquid phase boundaries are concerned.

The term of module will be used here to describe a functional group which is realised in hardware, software or as a combination of hardware and software.

The term of "identifier" will be used here for a code, a codeword, a signal, a memory entry or a flag which is set.

Reference is made to various laboratory appliances 100 in connection with the invention. They concern devices, systems, installations, apparatuses, handling centres and the like which are equipped with means for determining a phase boundary. The apparatus 110 in accordance with the invention is an element or a component of such a laboratory appliance 100. A laboratory appliance 100 can comprise several identical apparatuses 110 or several different apparatuses 110 for example.

The apparatus 110 in accordance with the invention is especially arranged for detecting a liquid level (i.e. a gas-liquid phase boundary) in a liquid container 5. This apparatus 110 can also be used for determining other phase boundaries. For the purpose of detecting it comprises a sensor 3 (e.g. in the form of a pipette tip or needle) which can be moved forward in the direction of the liquid 1 of the liquid container 5. A circuit 13 with circuit blocks 2, 7 and a controller module 8 is used which processes an output signal s(t) of the sensor 3 in order to detect a change in capacitance when reaching or penetrating the phase boundary. The circuit 13 comprises at least one first channel with a first filter in order to filter out a first signal $s1(t)$ of short pulse width from the output signal s(t). Furthermore, the circuit 13 comprises a second channel with a second filter in order to filter out a second signal $s2(t)$ of larger pulse width from the output signal s(t). The circuit 13 further comprises a controller module 8. Said controller module 8 comprises a comparator module which is configured in such a way that it can be determined whether the first signal $s1(t)$ reaches a first threshold value T1. The first threshold value T1 is predetermined by the apparatus 110 or the laboratory appliance 100. In addition to the first threshold value T1 it is also possible to determine and/or evaluate the pulse width P1. Furthermore, the control module 8 comprises a processing module which is arranged in such a way that it can be determined whether the second signal $s2(t)$ fulfils at least one predetermined second signal criterion (e.g. a minimum ascending gradient ST).

Figure 3:
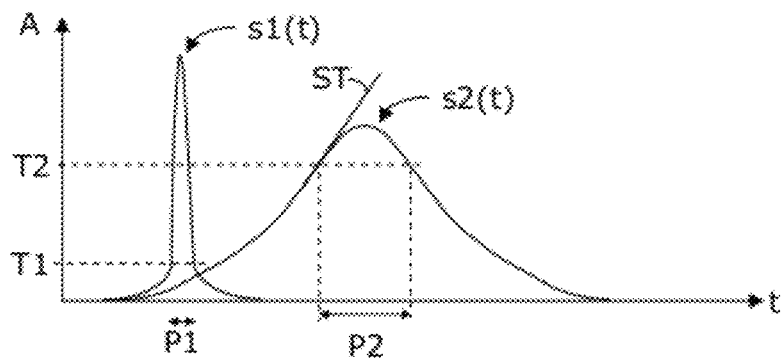
FIG. 3 shows a schematic amplitude-time diagram in which two signals in accordance with the invention are shown in a simplified form in order to enable the description of the application of criteria according to a first embodiment.

FIG. 3 shows a schematic amplitude-time diagram in which two signals $s1(t)$ and $s2(t)$ in accordance with the invention are shown in a simplified manner. The principal mode of operation of the various embodiments is described by reference to this exemplary illustration. By splitting the signal s(t) by means of 2 filters into a first signal $s1(t)$ and a second signal $s2(t)$, a much more precise statement can be made. Nevertheless it is still possible to respond directly on the basis of the first signal $s1(t)$. Such a direct reaction can be necessary in order to produce a stop of the advancing motion B after the detection of a signal s(t) which looks like an immersion signal in order to prevent immersion that is more than necessary. The reasons were already explained above. Preferably, the immersion depth is fixed at 2 mm.

FIG. 3 shows a first threshold value T1 at a relatively small amplitude A. In the simplest embodiment of the invention, it is only determined whether the first signal $s1(t)$ reaches this first threshold value T1. If this is the case, then the first criterion for a detection is regarded as being fulfilled.

In FIG. 3, a second threshold value T2 is set at an amplitude A which lies above the first threshold value T1. It is now determined whether the second signal $s2(t)$ fulfils at least one predetermined second signal criterion. In the simplest embodiment of the invention it is now determined whether the second signal $s2(t)$ reaches this second threshold value T2. If this is the case, then the second criterion for a detection is regarded as being fulfilled.

If the first signal criteria and the second signal criteria are fulfilled as described, the output (step 208 in FIG. 5) of an identifier (e.g. in the form of a signal or a code) can occur for example. Said identifier indicates that the apparatus 110 has performed a detection of a liquid level.

Notice must be taken that in the various embodiments of the invention the absolute values of the 2 threshold values T1 and T2 depend on the choice of further processing by circuitry. T1 can be smaller than, equal to or even larger than T2. For reasons of better clarity of the illustration, T2 is always chosen larger than T1 in the drawings.

Figure 11:
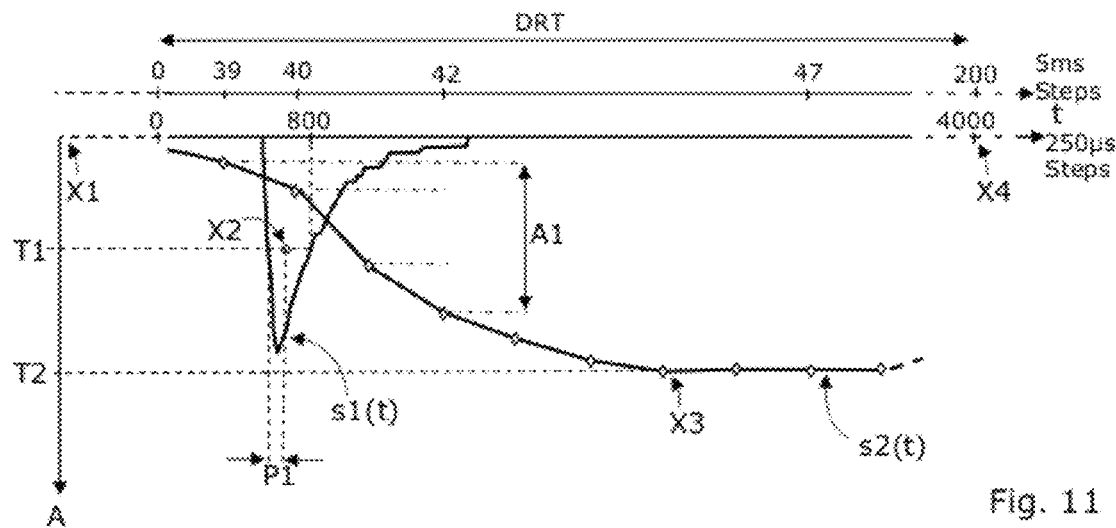
FIG. 11 shows a schematic amplitude-time diagram in which two signals in accordance with the invention are shown in order to enable the description of the application of criteria according to a further embodiment.

Optionally, the pulse width P1 can additionally be considered in the evaluation/processing of the first signal $s1(t)$ at the level of the first threshold value T1. In this case, the first signal criteria would comprise the first threshold value T1 and the pulse width P1. The risk of erroneous detections decreases by one or several additional criteria, which erroneous detections might occur as a result of electrostatic discharges for example. In FIG. 3, the pulse width P1 corresponds to the current pulse width of the signal $s1(t)$ at the level of the first threshold value T1. Since one might have to wait too long in this case until the entire pulse width P1 is detected, the pulse width P1 is set as a shorter time window in preferred embodiments. FIG. 11 respectively shows that such a shorter time window was specified as P1. This time window ends at point X2.

Notice is taken in the evaluation of the first signal $s1(t)$ and the definition of the first criterion or first criteria respectively that this evaluation is possible as rapidly as possible in order to enable a quick response.

Optionally, one or several of the following additional second signal criteria can be considered in the evaluation/processing of the second signal $s2(t)$ at the level of the second threshold value T2:

ascending gradient ST of the second signal $s2(t)$ in the threshold value T2 or at another point of the signal $s2(t)$, and/or
  pulse width P2 of the second signal $s2(t)$ in threshold value T2 or at another point of the signal $s2(t)$, and/or
  monotonous ascending gradient of the signal $s2(t)$ over several measuring points or over a time window.

Alternatively, the ascending gradient ST of the second signal $s2(t)$ or the pulse width P2 can be considered and evaluated at another point (e.g. at the level of threshold value T1) of the curve.

The mentioned first signal criteria and second signal criteria can be combined with one another at will as required.

The decision of detection can be improved by considering one or several additional signal criteria.

Figure 4:
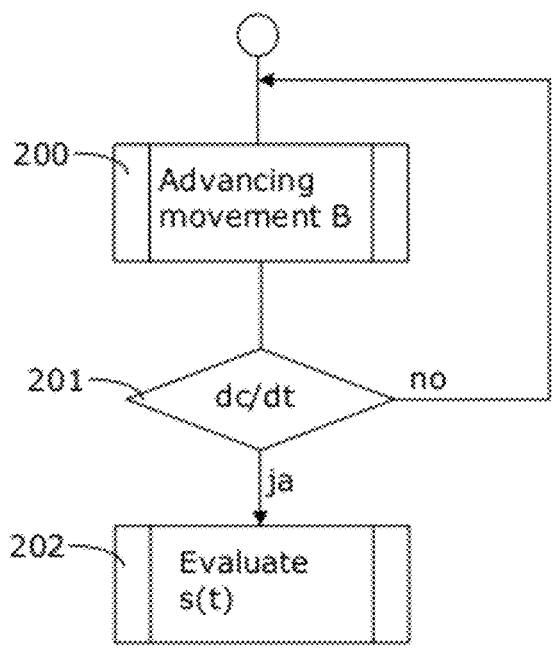
FIG. 4 shows a schematic flowchart of the operating principle of an apparatus in accordance with the invention.

The principle of operation of the apparatus 110 in accordance with the invention is described by reference to FIG. 4 which shows a schematic flowchart. Further details of the principle of operation of the signal evaluation of an apparatus 110 in accordance with the invention will be explained with reference to FIG. 5.

The apparatus 110 evaluates the output signal s(t) of the circuit 2 in order to enable the recognition of whether there is a change in the relative capacitance dc over time t or a small-time unit dt. Said step 201 is shown in FIG. 4 by the query dc/dt. The evaluation of the output signal s(t) is shown in FIG. 4 by the process 202. This evaluation occurs while the sensor 3 is advanced, which is illustrated in FIG. 4 by the process 200. The advancing movement B will be continued as long as there is no change in the relative capacitance dc. The advancing movement B can obviously be interrupted by the apparatus 110 or the laboratory appliance 100 when a maximally predetermined immersion depth Z-Max has been reached.

Figure 5:
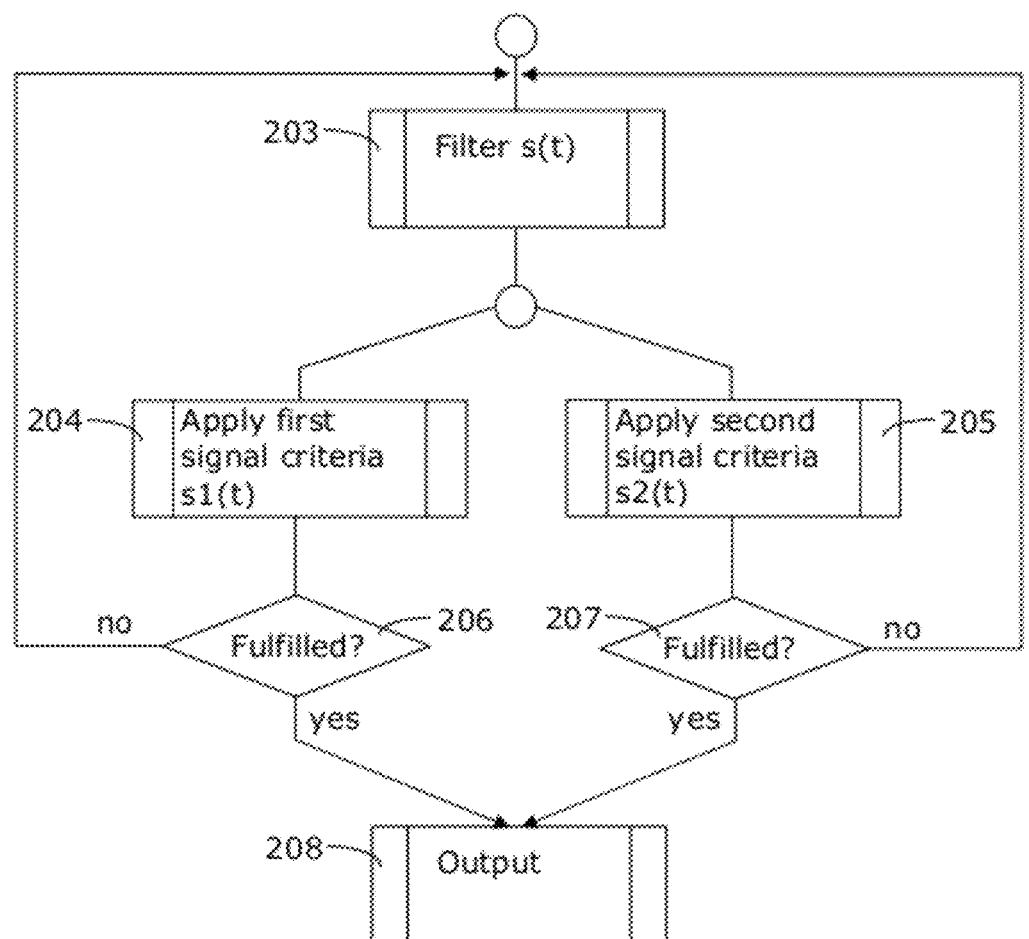
FIG. 5 shows a schematic flowchart of the operating principle of the signal evaluation of an apparatus in accordance with the invention.

Details of a method 202 for evaluating the signal s(t) are shown in FIG. 5. The signal s(t) is filtered in a first step 203 in order to obtain the aforementioned two signals $s1(t)$ and $s2(t)$. Thereafter, preferably simultaneously in all embodiments of the invention, the first signal criterion or criteria is/are applied to the first signal $s1(t)$ and the second signal criterion or criteria is/are applied to the second signal $s2(t)$, as indicated by the processes 204 and 205. Once the first signal criterion or criteria has/have been fulfilled, the decision-making process 206 will then issue a respective (success) signal. The same applies to the decision-making process 207. This process 207 issues a (success) signal when the second signal criterion or criteria has/have been fulfilled. In this case, a process 208 can issue an identifier (e.g. signal or code). If the first signal criterion or criteria is/are not fulfilled, the process branches back to the start. If the second signal criterion or criteria is/are not fulfilled, the process branches back to the start. If neither the first nor the second signal criterion or criteria should be fulfilled, the process also branches back to the start. The sequence can be performed repeatedly depending on the embodiment.

The method in accordance with the invention for detecting a phase boundary in a liquid container 5 therefore progresses as follows. A continuous or step-by-step advancing movement B (process 200) is performed in order to move the sensor 3 in the direction towards the liquid 1 in the liquid container 5. During this advancement B, there will be an evaluation 202 of the output signal s(t) of the sensor 3 in order to detect a change in capacitance dc/dt. During the evaluation 202, the output signal s(t) will be split by means of a first filter and the second filter (process 203). The filtering of the signals can also be realised in a common filter module. This leads to a first signal $s1(t)$ of short pulse width and a second signal $s2(t)$ of large pulse width.

It is then determined (processes 204, 206) whether the first signal $s1(t)$ corresponds to the predetermined first signal criterion or criteria (e.g. threshold value T1; or threshold value T1 and pulse width P1). It is also determined (processes 205, 207) whether the second signal $s2(t)$ corresponds to the predetermined second signal criterion or criteria (e.g. threshold value T2; or threshold value T2 and pulse width P2; or threshold value T2 and ascending gradient ST). If the first signal criterion or criteria and the second signal criterion or criteria are fulfilled, the output (process 208) of an identifier (e.g. a signal or a code) takes place which is representative of or indicates a detection of a phase boundary.

Figure 2:
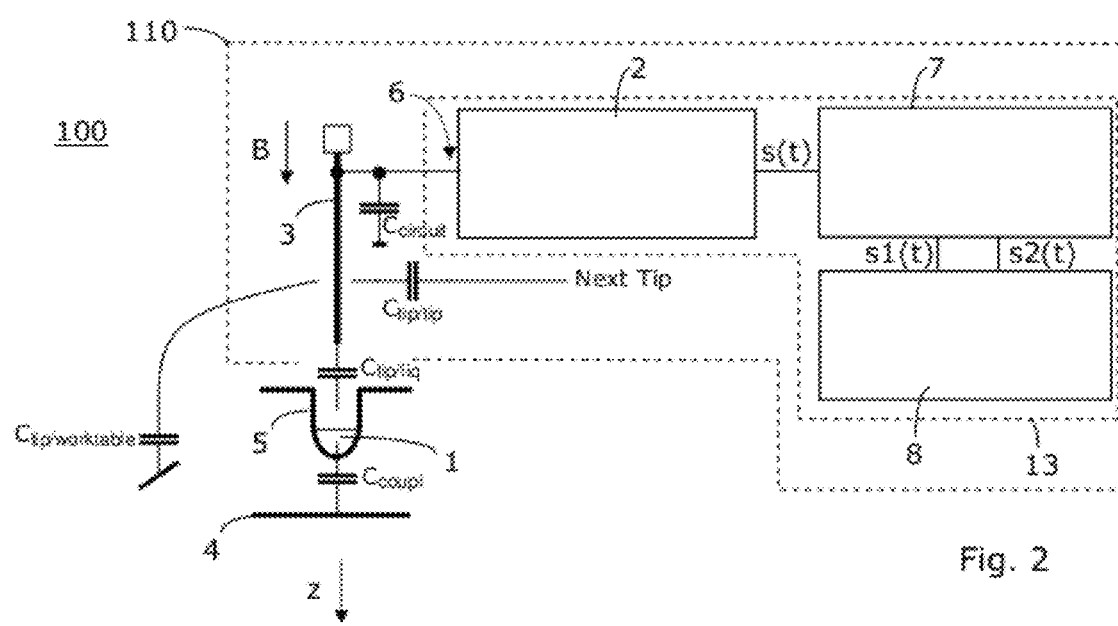
FIG. 2 shows a schematic side view of an apparatus in accordance with the invention with a circuit in accordance with the invention.
Figure 6:
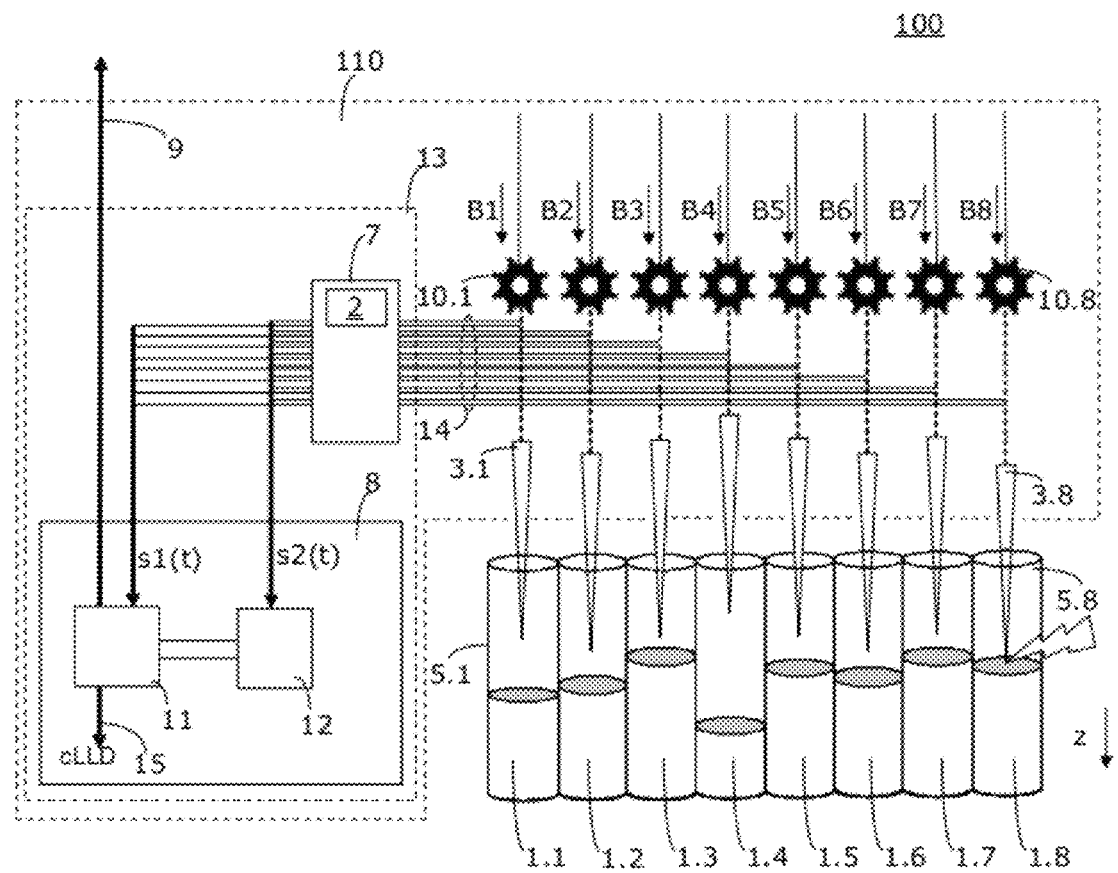
FIG. 6 shows a schematic side view of a further apparatus in accordance with the invention with a further circuit in accordance with the invention.

FIG. 6 shows a schematic side view of a further apparatus 110 in accordance with the invention comprising a further circuit in accordance with the invention. The details as described above can be applied to this embodiment. Therefore, the differences with the apparatus 110 according to FIG. 2 will mainly be described below. The laboratory appliance 100 comprises several channels in this case (eight channels here). Every channel comprises advancing means 10.1-10.8 which are illustrated here in a simplified way by gearwheels. The advancing means 10.1-10.8 produce a respective advancing movement B1-B8 which faces downwardly, as indicated by the arrows. The sensors 3.1-3.8 are advanced individually or jointly by the advancing means 10.1-10.8. The sensors 3.1-3.8 will submerge into the liquid container 5.1-5.8, which are all filled with liquids 1.1-1.8. The respective phase boundaries are indicated by the grey areas. In the illustrated moment, the sensor 3.8 dips into the liquid 1.8 of the liquid container 5.8. The relative change in capacitance which is obtained in the eighth channel of the apparatus 110 is represented here by a flash symbol. The sensors 3.1-3.8 of the individual channels are connected via lines 14 (preferably shielded lines) with the signal processing circuit 7. Said signal processing circuit 7 processes the signals s(t) of the individual channels separately. Every signal s(t) of each channel will be filtered in order to thereby obtain respective first and second signals $s1(t)$ and $s2(t)$. This means that eight first signals $s1(t)$ and eight second signals $s2(t)$ are obtained in total per measuring cycle. The sensors 3.1-3.8 are charged and discharged with a suitable frequency.

The apparatus 110 comprises a controller module 8, as is shown. The controller module 8 comprises a comparator module which is realised in this embodiment by a first microprocessor 11. The comparator module is arranged in such a way and the first microprocessor 11 is programmed in such a way that it determines whether the first signals $s1(t)$ of the individual channels reach the first threshold value T1. This principle has already been described above. In this case, the comparator module or the first microprocessor 11 processes all first signals $s1(t)$ of the eight channels successively in a staggered manner.

The controller module 8 further comprises a processing module which is realised in this embodiment by a second microprocessor 12. The processing module is arranged in such a way or the second microprocessor 12 is programmed in such a way that it determines whether the second signals $s2(t)$ fulfil predetermined second signal criteria. This principle has already been described above. In this case, the processing module or the second microprocessor 12 processes all second signals $s2(t)$ of the eight channels successively in a staggered manner. If both signals $s1(t)$ and $s2(t)$ meet the criteria for one of the eight channels, then it is assumed that the sensor 3 has reached the phase boundary to the liquid 1 in this channel. In this case, an identifier (e.g. in the form of a signal or a code) will be output for the eighth channel because the sensor 3.8 has just dipped into the liquid 1.8 in the container 5.8. This identifier can be output for example via an interface (cLLD) 15. The laboratory appliance 100 can make decisions, initiate reactions or the like on the basis of this identifier for example.

A common, highly powerful processor can also be used in the various embodiments instead of the two separate microprocessors 11 and 12.

Preferably, decisions are made by a suitable software in the various embodiments of the invention. For this purpose, the software receives information (e.g. the aforementioned identifier from the controller module 8 and signal values from a memory). Decisions can then be made on the basis of rules which are predetermined. The software can decide for example whether a sensor 3 (e.g. in the form of a needle or pipette tip) needs to be washed because it has been characterised as contaminated in accordance with the invention for example (see process 214 or 218 in FIG. 8 example). The software can also decide whether a channel should be switched off or whether operators should be called for example in case of an emergency.

It is indicated in FIG. 6 that the circuit 7 can comprise an electronic charging/discharging circuit 2. The electronic charging/discharging circuit 2 can also be provided at a different location. Moreover, the arrangement of this circuit 2 depends on which of the initially described capacitive measuring methods will specifically be applied.

Figure 7:
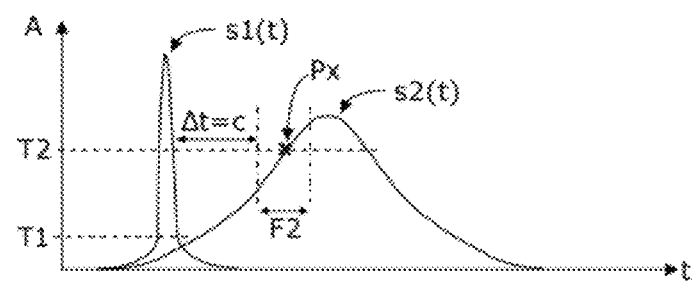
FIG. 7 shows a schematic amplitude-time diagram in which two signals in accordance with the invention are shown in a simplified form in order to enable the description of the application of criteria according to a further embodiment.

FIG. 7 shows a further schematic amplitude-time diagram in which two signals $s1(t)$ and $s2(t)$ in accordance with the invention are shown in a simplified way. This exemplary illustration is used to describe the fundamental principles of operation of a further embodiment. In this case too, there is a splitting of the signal s(t) by means of a common filter module or by means of two filter modules into a first signal s1(*t*) and a second signal s2(*t*).

A first threshold value T1 is set again at a relatively low amplitude A in FIG. 7. In the simplest of embodiments of the invention it is now determined whether the first signal s1(*t*) reaches said first threshold value T1. If this is the case, then the first criterion for a detection is regarded as being fulfilled.

A second threshold value T2 is set at an amplitude A in FIG. 7, which amplitude lies above the first threshold value T1. It is now determined whether the second signal s2(*t*) fulfils a to be determined second signal criterion. In the simplest of embodiments of the invention it is now determined whether the second signal s2(*t*) exceeds said second threshold value T2 within a time window F2. The time window F2 starts after a delay Δt=c. In the illustrated example the second signal s2(*t*) exceeds the threshold value T2 at the point of intersection Px which is marked with an "x". Since this point of intersection Px lies in the time window F2, the second criterion for a detection is regarded as being fulfilled.

If the first signal criterion or criteria and the second signal criterion or criteria are fulfilled as described, the output (step 208 in FIG. 5) of an identifier (e.g. in the form of a signal or a code) can occur and the downward movement can be stopped for example. This identifier indicates that the apparatus 110 has performed a detection of a phase boundary.

Figure 8:
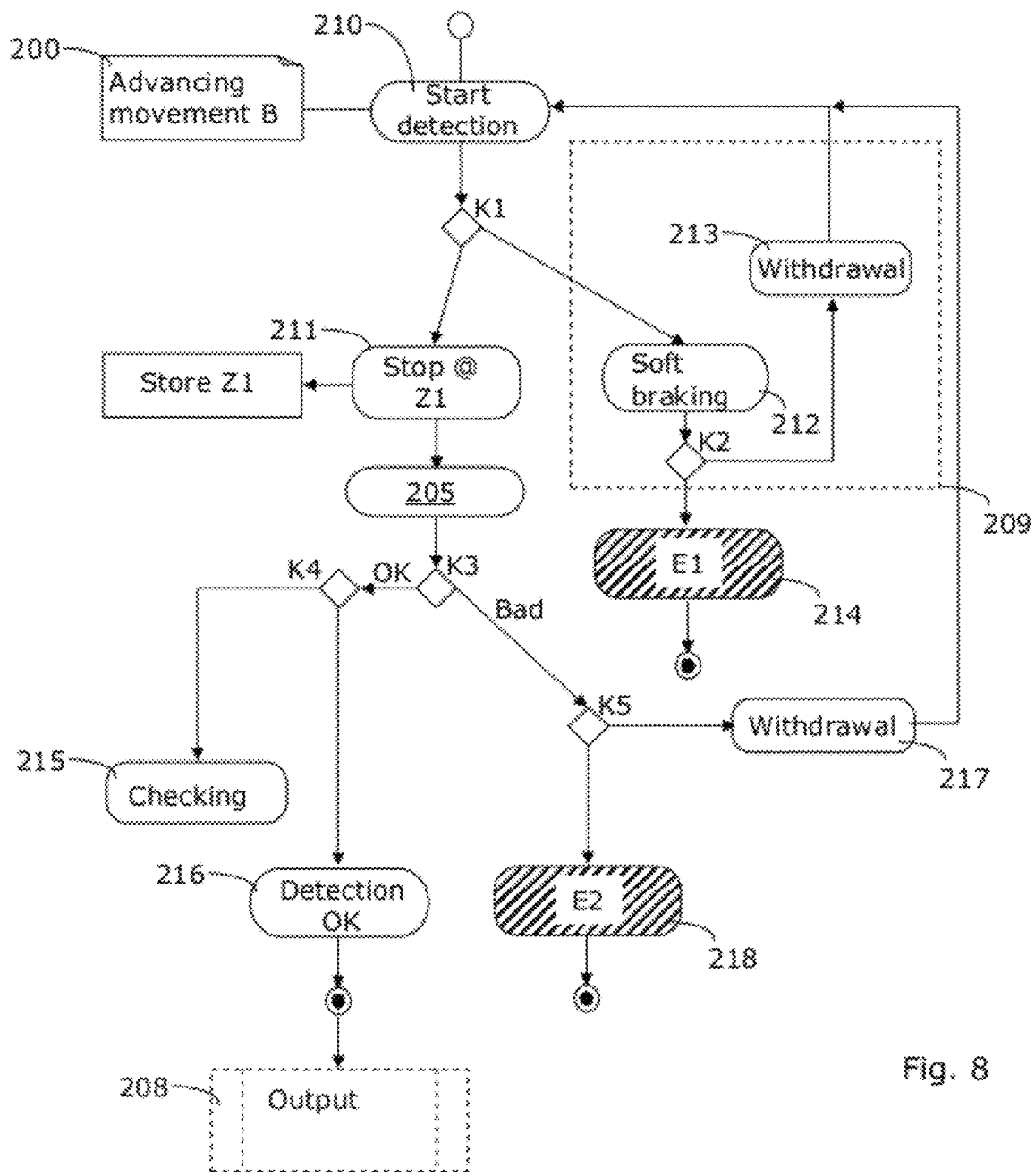
FIG. 8 shows a schematic flowchart of the operating principle of an exemplary method in accordance with the invention.

A further method in accordance with the invention is performed as shown in FIG. 8. An advancing movement B is performed (process 200). In this process, the respective sensor 3 performs a movement which starts at a starting position (Z start) and ends at the latest at a maximum (submerged) position (Z max). A movement profile can be provided here or the movement extends evenly at constant speed. Preferably, means are used in order to enable the determination of the absolute Z position of the sensor 3 at all times. As a result, maintaining the area Z start to Z max can be ensured at all times.

The process 210 indicates that the detection of a liquid level (LLD) is started here. At node K1 it is decided whether a rapid signal s1(*t*) was detected. If this was the case, then the method branches off in the direction of the process 211. The process 211 causes the immediate cessation of the advancing movement B in the current submerged position Z1 (submerged position, e.g. 2 mm beneath the phase boundary), which is followed by the process 205 for evaluating the slow signal s2(*t*). If only a slow signal s2(*t*) is detected at the node K1, the method branches in the direction of the process 212. Said process 212 is designated as a soft stop (soft braking). In this case, no abrupt stopping motion shall be performed. It is decided or verified at node K2 whether this concerns a one-off detection of only a slow signal s2(*t*). Node K2 preferably concerns a counter. In this case, process 213 will be applied. The process 213 predetermines that the sensor 3 is moved back by a small amount to the previous position. The process 210 will then be performed again. If only a slow signal s2(*t*) is detected again, the method again branches from K1 to process 212. At the node K2 the method will then branch to a process 214. The process 214 will output an error E1 (e.g. in the form of an error code). As part of the process 214 it is optionally possible that the determined data can be stored in a memory and/or the sample liquid 1 in the respective liquid container 5 and/or the sensor 3 can be marked and skipped (or switched off). The processes 212 and 213 are part of a special process or sequence which is adjusted to situations where only second slow signals s2(*t*) are detected.

When the main path of the method of K1 is followed by the process 211 and 205, a decision is made at node K3 whether the first criterion/first criteria is/are fulfilled by the first rapid signal s1(*t*) and also the second criterion/second criteria is/are fulfilled by the slow second signal s2(*t*). If this is the case, then the method branches at node K3 in the direction "OK". A query is made at node K4 whether the sensor 3 was flagged in anyway. Such flagging of the sensor 3 can occur in another preceding process. Accordingly, the sensor 3 could have been flagged as contaminated for example. In this case, the method branches at node K4 in the direction of the process 215. The process 215 can provide a (manual or automatic) check of the sensor 3. If the sensor 3 has not been flagged, the method ends with a successful detection (process 216) and the method can optionally enter the process 208 (also see FIG. 5).

If the decision was not OK at the node K3, the method branches at node K3 in the direction of a node K5. The node K5 can be arranged as counter. If the method according to FIG. 8 has branched once or twice successively at node K3 in the direction of node K5, process 217 will follow. As in the process 213, or in any other manner, a defined withdrawal of the sensor 3 can occur and the method will be repeated from process 210. If the method has branched 3 times successively at node K3 in the direction of node K5, an error E2 can be output by a process 218. The process 218 outputs an error E2 (e.g. in the form of an error code). As part of the process 218 it is optionally possible that the determined data can be stored in a memory and/or the sample liquid 1 in the respective liquid container 5 and/or the sensor 3 can be marked and skipped (or switched off).

The flow diagram according to FIG. 8 shall be understood as an example. The illustrated method can be modified depending on the laboratory appliance 100, the measuring method and the situation. It is also possible to provide further branches and routines for example in order to treat special cases.

Figure 9:
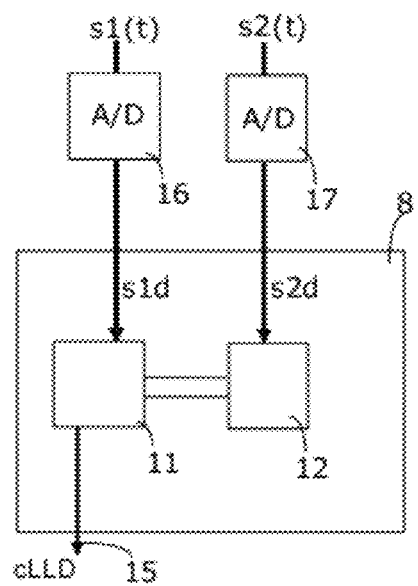
FIG. 9 shows a schematic block diagram which shows the conversion of the two analog signals $s1(t)$ and $s2(t)$ into the respective digital signals $s1d$ and $s2d$.

The apparatus 100 in accordance with the invention is preferably provided with two microprocessors 11 and 12, as shown in FIG. 6. A part of the signal processing of the signal s(t) preferably occurs in all embodiments of the invention in an analogous fashion. Preferably signal processing up to and with the two filter modules for providing the signals s1(*t*) and s2(*t*) is arranged in an analogous fashion. The conversion into digital occurs then by two separate analog-to-digital converters 16, 17 which are arranged before the microprocessors 11 and 12, as indicated in FIG. 9 in a schematic block diagram. Said analog-to-digital converters 16, 17 generate from the first analogous first signal s1(*t*) a first digitised signal s1*d* and from the analogous second signal s2(*t*) a second digitised signal s2*d*. Said signals s1*d* and s2*d* will then be processed by the controller module 8. If the apparatus 110 or the laboratory appliance 100 comprises several channels, the analog-to-digital converters 16, 17 are arranged accordingly.

Figure 10:
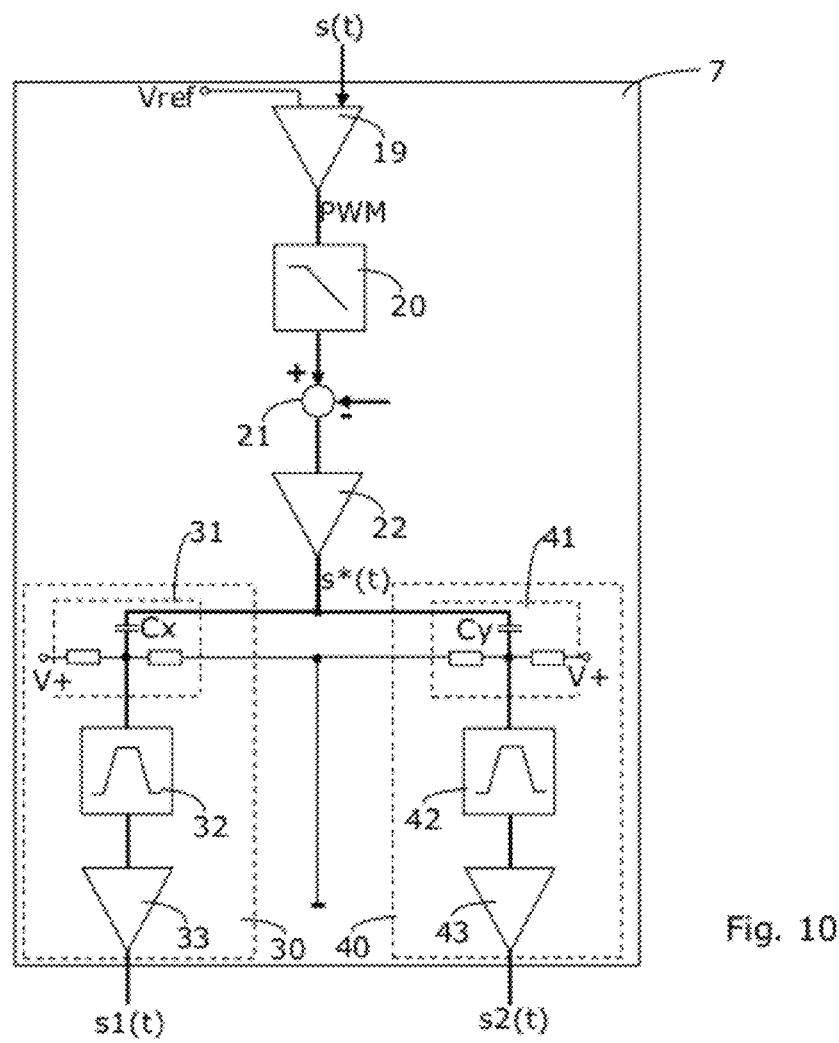
FIG. 10 shows a schematic block diagram of an embodiment of a signal processing circuit in accordance with the invention.

FIG. 10 shows a schematic block diagram of an embodiment of a signal processing circuit 7 in accordance with the invention. Said circuit 7 processes the signal s(t) which is tapped from the sensor 3. The circuit 2 can optionally be arranged between the sensor 3 and the circuit 7, depending on the measuring method and the overall concept of the apparatus 110. The circuit 7 assumes preparatory tasks for the evaluation (process 202) of the output signal s(t). This includes the splitting (process 203) of the output signal s(t) by means of a first filter module 30 and a second filter module 40 into a first signal s1(*t*) of short pulse width and a second signal s2(*t*) of larger pulse width, as already mentioned. The signal s(t) is preferably pretreated prior to said splitting (process 203). In this case, a comparator 19 can be used for example which places the signal s(t) in relation to a reference voltage Vref. A PWM (pulse-width modulated) signal is provided at the output of the comparator 19. The PWM signal shows a dependence on the momentary capacitance at sensor 3. Said PWM signal is processed by a filter module 20 (e.g. a Bessel filter of third order). An offset shift can then occur, as illustrated by the symbol with the reference numeral 21. A main amplifier 22 will finally follow in a preferable way. A signal is provided at the output of the main amplifier 22 which is designated here as an amplified signal s*(t). Said amplified signal s*(t) is now guided via two parallel filter modules 30 and 40, or via a common filter module. Both filter modules 30 and 40 comprise the following (as shown from input to output): a decoupler 31 and 41; a bandpass filter 32 and 42; a booster amplifier 33 and 43. The first decoupler 31 comprises a capacitor Cx on the input side and the second decoupler 41 comprises a capacitor Cy on the input side. The two decouplers 31 and 41 are arranged in such a way that they produce an alternating voltage decoupling. For this purpose, both decouplers respectively comprise a voltage divider with two resistors, as shown. The first bandpass filter 32 is characterised by the two frequencies f1=60 Hz and f2=1.8 kHz. The first booster amplifier 33 can have an amplification factor of between 10 and 20. The second bandpass filter 42 is characterised by the two frequencies f1=2.5 Hz and f2=18 Hz. The second booster amplifier 43 can have an amplification factor of between 11 and 15 for example.

The circuit according to FIG. 9 can follow the circuit according to FIG. 10 for example.

Preferably, at least a part of the sequence control of the method in accordance with the invention occurs by software. This software can be predetermined in the form of a firmware. Preferably, not only sequence control is realised by the software but also signal processing and evaluation. In this case, the respective modules are implemented by powerful processors with software.

The sequence control provides in the various embodiments that the advancing movement B in the direction of the Z axis will be stopped when reaching a phase boundary (stop @Z1, see FIG. 8). This means that when the detection of the first signal s1(t) or s1d is successful (see process 211), then the sequence control (process 211) preferably causes an immediate stop of the advancing movement B of the respective sensor 3. The sensor 3 is stopped immediately by the process 211 in order to prevent that the sensor 3 will be submerged more than is absolutely necessary. In this position Z1 the apparatus 110 will wait until it is determined whether the second signal s2(t) or s2d was also determined successfully. If the second criterion/second criteria is/are fulfilled for the second signal s2(t) or s2d, the detection will be regarded as being successful in its entirety (process 216).

The generation of the identifier (see process 208) can be performed by the second microprocessor 12 or a superordinate processor (not shown) can be used. Said superordinate processor can also assume other tasks for example.

Preferably, the apparatus 110 comprises a bus 9 (e.g. a controller area network bus; CAN bus) or the apparatus 110 can be connected with such a bus 9.

Before a detection method according to the invention will be applied or before the apparatus 110 will be used, a number of parameters will preferably be predetermined. (One or several of the following parameters can be defined (depending on the embodiment and respective application):

Setting the sensitivity (e.g. depending on the liquid to be detected).
Determining the first and/or second criterion/criteria.
Predetermining whether a special process (e.g. process 209 in FIG. 8) or detection mode will be used. It is optionally predetermined for one or several of the nodes how often the test shall be repeated. In the description of FIG. 8 only one single repetition was provided at node K2. This number can also be chosen differently for example.
Determination of reactions (e.g. reaction to successful detection; process 216).

These only concern examples. The above list can be extended. It is also possible to determine aspects for the aftertreatment after a detection.

FIG. 11 shows a further amplitude-time diagram in which two signals in accordance with the invention s1(t) and s2(t) of a specific liquid detection are shown. Aspects of further embodiments will be explained by reference to this illustration.

A first threshold value T1 is entered in FIG. 11 at a relatively low amplitude A. In the simplest embodiment of the invention, it is only determined whether the first signal s1(t) reaches said first threshold value T1. If this is the case, then the first criterion for a detection is regarded as being fulfilled. It is optionally possible here and also in all other embodiments to evaluate and consider the pulse width P1 and/or any other suitable criterion as the first criterion. In a preferred embodiment, the pulse width P1 is entered as a shorter time window, as in FIG. 11. FIG. 11 shows accordingly that such a shorter time window is determined as P1. This time window ends at point X2. It is inspected within this time window whether the signal s1(t) always remains above the threshold value T1. If this is the case, then this criterion is also fulfilled.

It is also possible to inspect whether the signal s1(t) has a maximum within such time window. This condition or this criterion would also be fulfilled in FIG. 11.

A second threshold value T2 at an amplitude A is entered in FIG. 11, which in the present case lies above (when the absolute values are regarded) of the first threshold value T1. It is now determined whether the second signal s2(t) fulfils a predetermined second signal criterion. In the simplest embodiment of the invention it is now determined whether the second signal s2(t) reaches said second threshold value T2. If this is the case, then the second criterion for a detection is regarded as being fulfilled.

If the first signal criterion/criteria and the second signal criterion/criteria are fulfilled as described, the output (step 208 in FIG. 5 or FIG. 8) of an identifier (e.g. in the form of a signal or code) can occur. Said identifier indicates that the apparatus 110 has performed a detection of a boundary surface.

The sequence of the method in accordance with the invention can occur as follows. The detection process will be started at a point X1 (process 210). The respective memory or registers of the apparatus 110 or the laboratory appliance 100 will be set to zero. A new rapid A/D value (which is also known as digital signal s1d) will be read in this example every 250 µs and the first criterion will be checked. It is checked at least whether the signal s1(t) or the respective digital signal s1d has reached the threshold value T1. Optionally, further first criteria (e.g. pulse width P1 and/or ascending gradient ST etc.) will be checked. During this process, a respectively rapid decoupler memory (shift register) will be filled with the digital signal s1d. A new slow A/D value (also known as digital signal s2d in this case) will be read every 5 ms in a parallel manner in this example and the second criterion or second criteria will be checked. It is checked at least whether the signal s2(t) or the respective digital signal s2d has reached the threshold value T2. Optionally, further second criteria (e.g. pulse width P2 and/or ascending gradient ST) will be checked. During this process, a respective further decoupler memory (e.g. shift register) will be filled with a digital signal s2d.

It was determined at a point X2 that a further criterion for the detection of the rapid signal s1(t) or s1d has been fulfilled (process 206). A stop signal will then be sent (process 211; stop@Z1) in order to stop the advancing movement (for the time being) at position Z1. The respective amplitude value of the rapid signal s1(t) or s1d will now be defined or marked in the rapid decoupler memory. The remainder of the rapid decoupler memory can be overwritten for example from the respective memory location. The values of the slow signal s2(t) or s2d can be defined marked in the further decoupler memory. The remainder of the further decoupler memory can be overwritten for example from this memory location. At this point in time, an optional value off-line can be set to "detection ongoing". In FIG. 8, the method is now in the region of the process 211, 205 and the node K3.

The slow signal s2(t) or s2d was evaluated (process 205) as described in order to determine whether the criterion or criteria for the second slow signal s2(t) or s2d are fulfilled. At point X3 the slow signal s2(t) or s2d will exceed the threshold value T2. The detection method can be regarded as being completed at point X4.

A further criterion is indicated in FIG. 11 by the double arrow A1 which can be applied to the second signal s2(t) or s2d. It can be predetermined for example that the signal s2(t) or s2d will rise monotonously from the first measured value (starting point of A1) up to the fourth measuring point (in point A1). The measuring points are shown here as small lozenges on the signal curve of the signal s2(t) or s2d.

Figure 12:
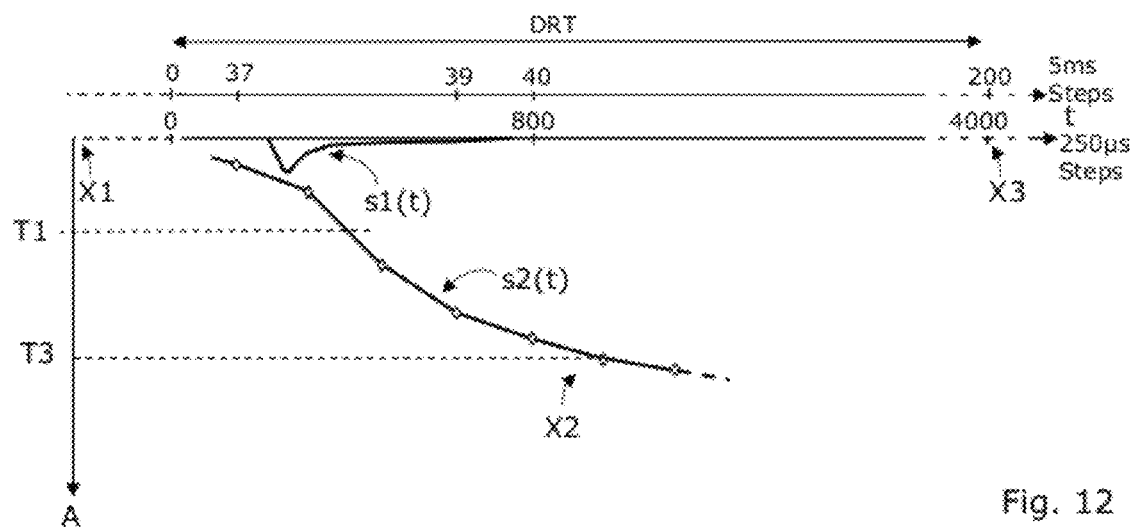
FIG. 12 shows a schematic amplitude-time diagram in which two signals in accordance with the invention are shown in order to enable the description of the application of criteria according to a further embodiment.

FIG. 12 shows the example of a detection method which was not completed successfully. The first rapid signal s1(t) or s1d is far too small and does not exceed the first threshold value T1 at any point in time. Nevertheless, a slow signal s2(t) or s2d occurs in this example which in principle would fulfil a second criterion because it exceeds the second threshold value T3 at point X2. A stop signal for a smooth braking process (e.g. according to process 212) will be set or transferred here at the latest at time X2 in order to interrupt the advancing movement B. In the flow chart according to FIG. 8, the method branches at node K1 in the direction of the special process 209.

The time window DRT for the recording (storing) of the digital signals s1d, s2d is one second in the illustrated examples of the FIGS. 11 and 12. In the illustrated example, the step width in the amplitude direction A is 4.2 mV and the step width on the first time axis is 250 µs, and 5 ms on the second time axis.

Depending on the embodiment, the comparison with the first threshold value T1 by the first microprocessor 11 can be implemented. The comparison therefore occurs in this case on the basis of the digitised first signal s1d. The comparison can also occur by means of the analog signal s1(t) and can be integrated for example as a functional block in the first filter module 30.

In an especially preferred embodiment, one of the filter modules 30, 40 or both filter modules 30, 40 are realised by means of software algorithms (like a soft filter). This offers the advantage that the filter functions which are applied can be adjusted. An implementation of the filter modules 30, 40 in the form of hardware as shown in FIG. 10 comes with the advantage that these filter modules 30, 40 work especially rapidly.

In an especially preferred embodiment, the two signals s1d and s2d are stored temporarily or permanently in order to perform their processing on the basis of stored values.

A stop of the advancing movement B can also be triggered depending on the embodiment when the slow second signal for example has an excessive ascending gradient ST.

The method or the apparatus 110 can send a report during the process execution or subsequently, which report contains information on the sequence of the process. This report can output the individual events together with the time values t, amplitude values A etc. in the form of a protocol.

In an especially preferred embodiment, the signals s1d and/or s2d are stored permanently or only in the case of special events (e.g. during the occurrence of one of the errors E1 or E2). In the latter case, considerably less memory space is "consumed".

In an especially preferred embodiment, both negative signals s1(t), s2(t) and also positive signals will be evaluated. The signals with negative preceding sign (see FIGS. 11 and 12 for example) can occur during the submersion of the sensor 3 for example, whereas signals with positive preceding sign can occur during surfacing for example. The consideration of positive and negative signals can also make sense when travelling through a phase boundary (depending on the direction of movement). Preferably, the surfacing signals will be evaluated in a similar manner as shown in FIG. 8. The respective reactions and branch-offs can be provided differently however. Furthermore, other criteria for signal processing will preferably be applied in the evaluation/processing of the surfacing signals.

A consideration of the preceding sign can also supply important information for example when a laboratory appliance 100 is concerned which aspirates liquid 1 from a liquid container 5 and in which the detection of a phase boundary according to the invention is performed. During the aspiration, the liquid level in the liquid container 5 will drop and the needle or the sensor 3 will follow. When the needle or the sensor 3 follows too slowly, the special case can occur that the needle or the sensor 3 will suddenly emerge from the liquid 1 again. As a result of an evaluation of the signal s(t) which occurs during the surfacing and by taking the preceding sign of this signal s(t) into account, the apparatus 110 can recognise that unexpected surfacing has occurred. Respective measures can be initiated in this special case.

In an especially preferred embodiment, a sensitivity measuring method is preferably applied in a preparatory step by using the sensor 3 and the circuit 2, 7, 8 in order to enable performing an automated setting of parameters and/or criteria on the basis of the liquid properties determined in this manner (such as conductivity and/or permittivity). An automatic setting of the apparatus 110 and/or the laboratory appliance 100 can be performed in this manner depending on the properties of the liquid to be detected (e.g. according to conductivity). Predefined settings of any kind and combination of liquids 1, sensors 3, the board 3 appliances 100 etc. can therefore be performed in this embodiment. As a result of an adjustment to the properties of the liquid, real signals can be differentiated in a better way from disturbing signals and interferences. The detection precision will be improved thereby. Furthermore, fewer manual interventions are required.

In a sensitivity measuring method in accordance with the invention it is utilised that most liquids can be classified in groups and that each of these groups has characteristic properties. Preferably, the first criterion which in this case is the threshold value T1 will be determined set on the basis of a sensitivity measuring method in accordance with the invention. The other criteria for evaluating/processing the first signal s1(t) and/or the second signal s2(t) can then be derived automatically from the threshold value T1 or queried from a table.

It is one advantage of a combination of the detection method in accordance with the invention with the sensitivity measuring method in accordance with the invention that reliable and highly sensitive measurements are enabled with minimum input of the user of the apparatus 110 or the laboratory appliance 100. The conductivity had been determined manually up until now with a conductivity measuring device for example. Conductivity measurements are often performed in separate containers, leading to an increased consumption of the often very expensive reagents.

In an especially preferred embodiment, the reference voltage will be set for example according to the respective Z position of the sensor 3. A dependence on the advanced position can be predetermined or compensated thereby. This setting can also occur continuously step-by-step. The setting can also be chosen depending on the geometry of the liquid container 5 and/or the properties of the liquid 1. The sensitivity is preferably set as a function of the Z position in order to enable the precise detection of small (residual) quantities for example. Furthermore, it is possible by providing changing criteria, threshold values or parameters with increasing advancing depth that disturbances occur as a result of an excessively large initial sensitivity.

More than just two filter modules 30, 40 are used in a further embodiment. Further signals of different properties are available thereby, the evaluation of which enables providing further information in connection with the liquid detection.

It is one advantage of the detection method in accordance with the invention that a differentiation is enabled between a true detection signal s(t) and an artificial signal which is produced by electrostatic discharge for example (e.g. as a result of parasitic induction).

Examinations have shown that the analog signals $s1(t)$ and $s2(t)$, and the digital signals $s1d$ and $s2d$ respectively, are self-similar, which means the signal shape is similar. This property can be used in order to calculate in advance the expected curve of a signal (e.g. by extrapolation). In this case, it is not necessary to wait until the end of the signal. Instead, conclusions can already be drawn at an earlier point in time. This is indicated in FIG. 11 by way of the pulse width P1 or the reduced time window. The knowledge is utilised in this case that the signal $s1(t)$ is a "real" detection signal with a high amount of probability when it continues to rise within the time window for example.

The self-similarity of the signals also enables a further digital evaluation of the signals. A rapid comparison of the currently determined signals with stored setpoint signals can occur in order to rapidly recognise (e.g. at an early point in time) a successful detection.

The self-similarity of the signals also enables an improved digital evaluation of the second signal node $s2(t)$ or $s2d$ for example. The curve of the signal $s1(t)$ or $s1d$ allows drawing conclusions on the expected properties of the second signal $s2(t)$ or $s2d$. This allows an adjustment (of the settings) of the second filter module 44 example.

Special cases can also be recognised and treated on the basis of a digital evaluation of the signals $s1d$ and $s2d$.

In an especially preferred embodiment, so-called libraries are created which the laboratory appliance 100 or the apparatus 110 can access. For this purpose, the digitised signals (e.g. $s1d$ and/or $s2d$) can be stored. Self-learning or at least adaptable solutions can be realised in this manner.

In an especially preferred embodiment, the raw data (e.g. the signals $s1d$ and/or $s2d$) and optionally other data (e.g. Z position etc.) will be saved. Other processes and devices (e.g. the laboratory appliance 100) can be arranged in such a way that they are able to access this data.

In other embodiments to which the aforementioned can be applied 1:1, either an oscillating circuit is used instead of a charging/discharging circuit 2, the frequency of which will change with changing effective capacitance at the sensor 3, or a circuit will be used in order to detect the changing capacitance (dc/dt) on the basis of a change in the phase, voltage or current.

The invention of the various embodiments can be applied to single-channel laboratory appliances 100 and also to multi-channel laboratory appliances 100.

Preferably, the apparatus 110 comprises an error code generator in order to enable the output of an error code (e.g. E1 and E2) for further processing depending on the situation.

The output (process 208 FIG. 5) occurs in such a way that further processing is possible by another process or another element of the apparatus 110 or the laboratory appliance 100 (e.g. a control system or computer).

LIST OF REFERENCE NUMERALS

Liquid 1
Liquids of individual channels 1.1-1.8
Electronic charging/discharging circuit 2
Advanceable sensor (e.g. pipette tip) 3, 3.1-3.8
Base plate 4
Liquid container 5
Liquid container of individual channels 5.1-5.8
Input side 6
Signal processing circuit 7
Controller module 8
Bus 9
Advancing means (e.g. DC motors) 10, 10.1-10.8
First microprocessor 11
Second microprocessor 12
Circuit 13
Lines 14
Interface 15
First analog-to-digital converter 16
Second analog-to-digital converter 17
(CAN) Bus 18
Comparator 19
Filter module 20
Offset shift 21
Main amplifier 22
First filter module 30
First decoupler 31
First bandpass filter 32
First booster amplifier 33
Second filter module 40
Second decoupler 41
Second bandpass filter 42
Second booster amplifier 43
Laboratory appliance 100
Apparatus 110
Advancing movement 200
Query dc/dt 201
Evaluation of an output signal 202
s(t) filtering 203
Apply first signal criterion to $s1(t)$ 204
Apply second signal criterion to $s2(t)$ 205
Check whether criteria are fulfilled 206
Check whether criteria are fulfilled 207
Output of an identifier 208
Soft braking due to slow signal $s2(t)$ 209
Start of detection 210
Stop at submerged position Z1 211
Stop 212
Withdrawal 213
Output error code E1 214

Check the sensor 215
Detection OK 216
Withdrawal 217
Output error code E2 218
Amplitude A
Further criterion A1
Advancing movement B
Advancing movement of individual channels B1-B8
Parameter c
Change in capacitance $C_{meas}$
Stray capacitance $C_{tip/tip}$
Coupling capacitor $C_{coupl}$
Capacitance between sensor and liquid $C_{tip/liq}$
Capacitance between sensor and liquid during submerging $C_{tip/liq\text{-}in}$
Capacitance between sensor and liquid with non-submerged sensor $C_{tip/liq\text{-}out}$
Coupling capacitor $C_{coupl}$
Capacitance between sensor and worktable $C_{tip/worktable}$
Capacitance of cable $C_{cable}$
Capacitance of filter circuit $C_{filter}$
Total capacitances $C_{total}$
Change in capacitance $\Delta C$ or dc/dt
Relative capacitance dc
Relative time or time unit dt
Data recording time window DRT
Error E1, E2
Frequencies of the filters f1, f2
Time window F2
Nodes K1, K2, K3, K4, K5
Pulse width P1, P2
Point of intersection Px
Output signal s(t)
Amplified signal s*t
First signal s1(t)
First signal, ditigized s1d
Second signal s2(t)
Second signal, digitized s2d
Ascending gradient ST
Reference voltage Vref
Operating voltage V+
Points X1, X2, X3, X4
Axis z
Submerged position Z1
Starting position Z-Start
Maximum (submerged) position Z-Max
Delay Δt
Time t
First threshold value T1
Second threshold value T2
Further threshold value T3

The invention claimed is:

1. A method for detecting a phase boundary between two media in a liquid container (5) with a sensor (3) which produces a change in capacitance (dc/DT) upon reaching the phase boundary, with the method comprising the following steps:
   a. performing (200) an advancing movement (B) in order to move the sensor (3) in the direction towards the phase boundary (1);
   b. evaluating (202) an output signal (s(t)) of the sensor (3) in order to detect a change in capacitance (dc/DT); characterized by the following steps:
   c. upon evaluating (202) the output signal (s(t)), splitting (203) of the output signal (s(t)) by means of a first filter method into a first signal (s1(t), s1d) of short pulse width and by means of a second filter method into a second signal (s2(t), s2d) of larger pulse width;
   d. determining (204, 206) whether the first signal (s1(t), s1d) fulfils a predetermined first signal criterion (T1, P1);
   e. determining (205, 207) whether the second signal (s2(t), s2d) fulfils a predetermined second signal criterion (T2, P2, ST, A1), and
   f. if the first signal criterion (T1, P1) and the second signal criterion (T2, P2, ST, A1) are fulfilled, output (208) of an identifier which represents or indicates a detection of a phase boundary.

2. A method according to claim 1, characterized in that the sensor (3) is repeatedly electrically charged and discharged at least during the performance of step a. (200).

3. A method according to claim 1, characterized in that the steps b. to e. are repeated until in step f. the fulfillment of the first signal criterion (T1, P1) and the second signal criterion (T2, P2, ST, A1) has been determined, with the advancing movement (B) being performed further during the repetition of the steps b. to e.

4. A method according to claim 1, characterized in that it is determined in step e. as the second signal criterion (T2, P2, ST, A1) whether the second signal (s2(t), s2d) rises continuously.

5. A method according to claim 4, characterized in that it is determined in step e. as the further second signal criterion (T2, P2, ST, A1) whether the second signal (s2(t), s2d) reaches a threshold value (T2) in a predetermined period of time (F2).

6. A method according to claim 1, characterized in that it is determined in step d. as the first signal criterion (T1, P1)
   whether the first signal (s1(t), s1d) reaches a first threshold value (T1), and/or
   whether a pulse width of the first signal (s1(t), s1d) reaches a minimum pulse width (P1), and/or
   whether the first signal (s1(t), s1d) rises during a predetermined time window, with step d.) being repeated in predetermined first time intervals.

7. A method according to claim 1, characterized in that the advancing movement (B) of the sensor (3) is braked smoothly if the second signal (s2(t), s2d) fulfils a further signal criterion (ST; T3) in step e) without the first signal (s1(t), s1d) having fulfilled the first signal criterion (T1, P1) in step d.

8. A method according to claim 1, characterized in that the preceding signs of the first signal (s1(t), s1d) and/or the second signal (s2(t), s2d) are also determined during the steps d. and e. in order to thereafter identify in a further step on the basis of the preceding sign a submerging of the sensor (3) into the liquid (1) or a surfacing of the sensor (3) from the liquid (1) or the passing of a phase boundary.

9. A method according to claim 1, characterized in that a sensitivity measurement process is performed by using the sensor (3) and the circuit (2; 7, 8), in order to perform on the basis of liquid properties thus determined an automated presetting of a threshold value, parameter or criterion of the circuit (2; 7, 8) in a further step.

10. A method according to claim 1, characterized in that a setting of the threshold value, parameter or criterion is performed on the basis of the current position of the sensor (3).

11. A method according to claim 1, characterized with the predetermined first signal criterion (T1, P1) being applied simultaneously to the first signal (S1(+), S1d) and the predetermined second signal criterion (T2, P2, ST, A1) to the second signal (S2(+), S2d).

12. A method according to claim 9, characterized by using the sensor (3) and the circuit (2; 7, 8) in a preparatory step.

13. Apparatus (110) for detecting a phase boundary between two media in a liquid container (5), comprising
- a sensor (3) which can be advanced in the direction of the phase boundary;
- a circuit (2; 7, 8) which processes an output signal (s(t)) of the sensor (3) in order to detect a change in capacitance (dc/DT);

characterized in that the circuit (2; 7, 8) comprises the following:
- a first channel with a first filter module (30) in order to filter a first signal (s1(t), s1d) of short pulse width from the output signal (s(t));
- a second channel with a second filter module (40) in order to filter a second signal (s2(t), s2d) of larger pulse width from the output signal (s(t));
- a controller module, comprising
- a comparator module (11) which is arranged in such a way that it can be determined whether the first signal (s1(t), s1d) reaches a first threshold value (T1), and comprising
- a processing module (12) which is arranged in such a way that it can be determined whether the second signal (s2(t), s2d) fulfils at least one predetermined second signal criterion (T2, P2, ST, A1).

14. Apparatus (110) according to claim 13, characterized in that the first filter module (30) and the second filter module (40) are realized in hardware and two analog-to-digital converters (16, 17) are provided in order to digitize the first signal (s1(t)) and the second signal (s2(t)) separately before a first digitized signal (s1d) and a second digitized signal (s2d) are processed by the controller module (8).

15. Apparatus (110) according to claim 14, characterized in that the controller module (8) comprises two microprocessors (11, 12), with a first one of the two microprocessors (11) being arranged for processing the first digitized signal (s1d) and the other of the two microprocessors (12) being arranged for processing the second digitized signal (s2d).

16. Apparatus (110) according to claim 13, characterized in that it comprises a module for the determination of properties of the liquid, with said module being convertible to the circuit (2; 7, 8) in order to enable performing an automatic sensitivity setting of the circuit (2; 7, 8).

17. Apparatus (110) according to claim 14, characterized in that the controller module (8) comprises two buffer memories in order to intermediately store first digitized signals (s1d) and second digitized signals (s2d).

18. Apparatus (110) according to claim 13, characterized in that it comprises an error code generator in order to enable the output of an error code (E1, E2) for further processing depending on the situation.

19. Apparatus (110) according to claim 13, characterized in that it comprises a switching element in order to charge and discharge the sensor (3) several times.

20. Apparatus (110) according to claim 13, characterized in that it
- comprises an oscillation circuit, the frequency of which changes with changing effective capacitance on the sensor (3), or
- comprises a circuit in order to detect the change in capacitance (dc/DT) on the basis of a change in the phase, voltage or current.

21. Laboratory appliance which comprises at least one apparatus (110) according to claim 13.

* * * * *